(12) United States Patent
Yao (10) Patent No.: US 9,642,583 B2
(45) Date of Patent: May 9, 2017

(54) DISPOSABLE SHEATH FOR DENTAL DIRECT IMAGING DIGITAL DEVICE

(71) Applicant: DENSMART DENTAL CO., LTD., Taoyuan Hsien (TW)

(72) Inventor: Yin Chao Yao, Taoyuan Hsien (TW)

(73) Assignee: DENSMART DENTAL CO., LTD., Taoyuan Hsien (TW)

( * ) Notice: Subject to any disclaimer, the term of this patent is extended or adjusted under 35 U.S.C. 154(b) by 196 days.

(21) Appl. No.: 14/583,489

(22) Filed: Dec. 26, 2014

(65) Prior Publication Data

US 2015/0257721 A1    Sep. 17, 2015

(30) Foreign Application Priority Data

Mar. 14, 2014    (TW) .............................. 103109351 A (51) Int. Cl.
*H01J 31/49*    (2006.01)
*A61B 6/14*    (2006.01)
*A61B 6/00*    (2006.01)

(52) U.S. Cl.
CPC ............ *A61B 6/145* (2013.01); *A61B 6/4423* (2013.01); *A61B 2562/247* (2013.01)

(58) Field of Classification Search
CPC . A61B 2562/247; A61B 6/145; A61B 6/4423; A61B 1/00165; A61B 1/0017;
(Continued)

(56) References Cited

U.S. PATENT DOCUMENTS

| | | | |
|---|---|---|---|
| 7,261,463 B2* | 8/2007 | Becht ..................... | A61B 6/145 378/168 |
| 2003/0152196 A1* | 8/2003 | Bratslavsky ........... | A61B 6/145 378/170 |

(Continued)

*Primary Examiner* — Irakli Kiknadze
(74) *Attorney, Agent, or Firm* — Rabin & Berdo, P.C.

(57) ABSTRACT

The present invention provides a sheath for a disposable dental direct imaging digital device. The sheath for a disposable dental direct imaging digital device includes a bag structure that is made up of an elastic material, and is also made up of a positioning device that is placed in an opening of the bag structure. A direct imaging digital device may be inserted into the sheath. A first housing segment that is in connection with the opening exists on one end of the bag structure. The other end of the first housing segment is in connection with a second housing segment. A tapered channel is formed from the opening of the first housing segment towards the second housing segment. A positioning device may close or shrink the opening, so as to prevent the direct imaging digital device from sliding out of the sheath. The direct imaging digital device may be inserted into the first housing segment, and then may be inserted into the second housing segment. Accordingly, the direct imaging digital device may be encapsulated and positioned by the second housing segment. In accordance with the present invention, the time of insertion the direct imaging digital device into the sheath may be shortened, and ease of use of the sheath with the direct imaging digital device may be enhanced. Moreover, the sheath of the present invention may be suitable for a direct imaging digital device of any size.

13 Claims, 8 Drawing Sheets

(58) Field of Classification Search
CPC ......... A61B 1/24; A61B 1/247; A61B 5/0071;
A61B 5/0088; A61B 5/742; A61B 1/32;
A61B 6/14; A61B 6/4233; A61B 6/4452;
A61B 6/548; A61B 6/563; A61C 9/0006;
A61C 9/0053; A61C 9/0073; A61C
9/0093; A61C 17/04; A61C 19/003; A61C
1/088; A61C 5/122; A23L 11/20; A23L
27/12; A23L 27/24; A23L 27/50; A23L
11/09; A23L 1/202; A23L 7/104; A23L
7/1975; G03B 42/02
USPC .................................. 378/167–175, 189–191
See application file for complete search history.

(56) References Cited

U.S. PATENT DOCUMENTS

| | | | | |
|---|---|---|---|---|
| 2005/0265522 | A1* | 12/2005 | Manley | G03B 42/02 378/169 |
| 2007/0130889 | A1* | 6/2007 | Wilson | B65D 33/04 53/467 |
| 2011/0017619 | A1* | 1/2011 | Motoyama | A61B 6/14 206/305 |

* cited by examiner

FIG. 8 ately placed into a sheath, since the size of the sheath is slightly larger than the size of the direct imaging digital device, makes the insertion difficult, and such an inser-

DISPOSABLE SHEATH FOR DENTAL DIRECT IMAGING DIGITAL DEVICE

FIELD OF THE INVENTION

The present invention relates generally to a sheath for housing a dental direct imaging digital device, and more particularly, the present invention relates to a disposable sheath for a dental direct imaging digital device that enables a dentist or a health care professional to conveniently place a direct imaging sensing device into the disposable sheath; in other words, the sheath can be disposed after a photo has been taken of the patient's teeth.

BACKGROUND OF THE INVENTION

Nowadays, a patient may see a dentist in a major hospital or a small dental clinic for treatment. For example, a dentist or a health care professional can carry out oral dental X-ray photography in a secure and isolated room or space that is equipped with professional digital X-rays during the patient's first visit to the dentist, for the purposes of a regular check-up or for checking any abnormalities which cause discomfort to the patient. The dentist can thus clearly see the general status of and the relative distribution of the patient's teeth.

Figure 1:
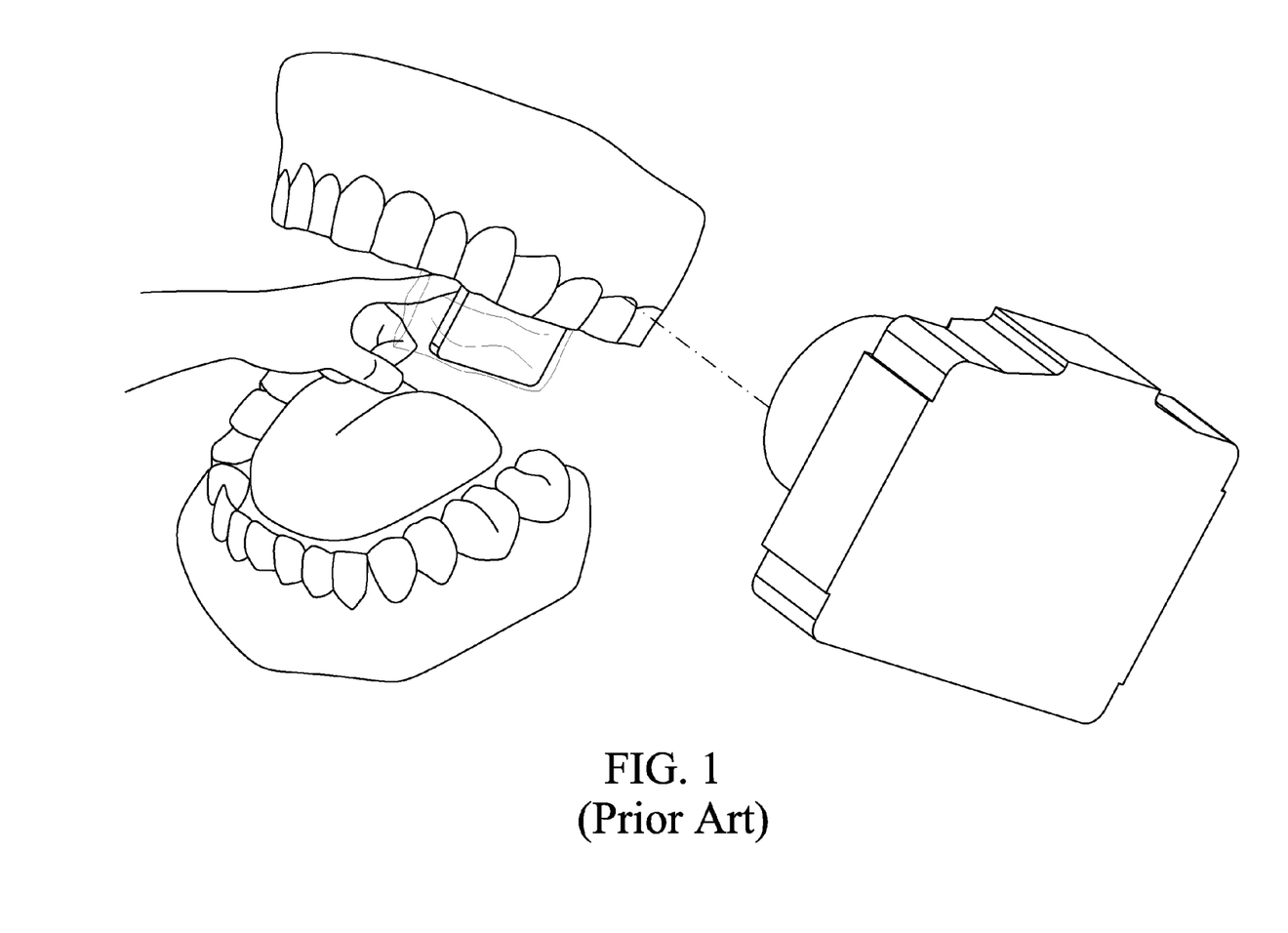
FIG. 1 is a three-dimensional schematic diagram of a conventional direct imaging digital device placed into a patient's oral cavity.

Once the patient enters the isolated and secure room or a space that is equipped with professional digital X-rays, the patient is then requested to be standing or seated in a fixed position in front of the X-ray equipment. The patient needs to wear protective clothing since the torso part of the body needs to be shielded from the X-ray irradiation. Referring to FIG. 1, FIG. 1 shows an imaging film that is used to show the results of X-ray irradiation (this may also be known as direct digital imaging digital device), and this imaging film will be placed into the oral cavity of the patient. In particular, the imaging film will be placed at specific areas of the oral cavity having teeth that cause discomfort to the patient. The imaging film needs to be pressed on the teeth that cause discomfort either by the dentist, the health care professional or by the patient. Moreover, the imaging film needs to be fixed in the patient's oral cavity, either by means of the patient biting on the imaging film, or it may be fixed by means of an assisting device. Subsequent to fixing the imaging device, an image will be taken by X-rays such that the image result is produced on the direct imaging digital device. The dentist may directly see the image result on a computer monitor, such that the dentist can offer an explanation on the status of the patient's teeth. Furthermore, the dentist may also be able to find out any dental diseases of the patient. In addition, such imaging results may also be referred to on numerous later occasions by the dentist if necessary.

Among such instant X-ray image irradiation technologies, the direct imaging digital device is a relatively expensive medical material, but the direct imaging digital device cannot be disinfected by high temperature and high pressure, or soaked in disinfectant methods. In order for the direct imaging digital device to be re-used and not let the direct imaging digital device be wasted, and also being able to avoid oral health and safety issues of individual patients in the meantime, a sheath is then developed which is suitable for covering the direct imaging digital device.

The size of the opening of the traditional sheath is very similar to the size of the direct imaging digital device. As such, when the dentist or the health care professional inserts the direct imaging digital device into the sheath, the insertion is very time-consuming because the alignment of the direct imaging digital device and the sheath is difficult to be achieved.

Furthermore, different manufacturers may produce different direct imaging digital devices and sensing devices that have different sizes and specifications. However, the traditional sheath is only suitable for a single-sized direct imaging digital device. Accordingly, hospitals or dental clinics may be required to buy sheaths having different sizes. This causes great inconvenience and may increase the medical costs.

SUMMARY OF THE INVENTION

The main objective of the present invention is to provide a sheath for encapsulating a dental direct imaging digital device. The sheath for encapsulating the dental direct imaging digital device has been designed in a manner such that it has a slightly larger diameter; moreover, the sheath for encapsulating the dental direct imaging digital device may be designed such that it has a tapered structure, to enable the direct imaging digital device to be able to move to the positioning end of the sheath for encapsulating the dental direct imaging digital device. The direct imaging digital device may be securely encapsulated and positioned; this may bring a lot of convenience to dentists and other health care professionals, since these professionals may directly place the direct imaging digital device into the interior of the sheath. As such, the design of the sheath may be designed such that the ease of use of the sheath for a direct imaging digital device may be significantly enhanced.

The other objective of the present invention is to enable the sheath to be made of an elastic material, and by means of an elastic expansion, the one-sized sheath may be able to suitably encapsulate the direct imaging digital device of various sizes, and as such, significantly increasing the breadth of applications of the sheath for a direct imaging digital device.

An additional objective of the present invention is to have a positioning device that may enable the opening of the sheath to be made smaller as necessary, or relatively speaking, that may enable the opening to be closed. The aforesaid design enables the length of the sheath to partially decrease, and also enabling the surface area of the sheath to be reduced as necessary, so as to reduce discomfort for the patient when the sheath for a direct imaging digital device is inserted into the oral cavity of the patient. In addition, the aforesaid design may also prevent the direct imaging digital device to slip out from the interior of the sheath.

In order to achieve the aforesaid objective, the sheath of the present invention may be made up of a first sheet body that is in connection with a peripheral edge of a symmetrical second sheet body, and thus forming a bag structure with an opening; and a direct imaging digital device may be positioned in the interior of the bag structure. Accordingly, the direct imaging digital device and the sheath for encapsulating the direct imaging digital device are placed into the oral cavity of the patient. A first housing segment that is in connection with an opening exists on one end of the bag structure, the other end of the first housing segment may be in connection with a second housing segment, wherein the size of the opening may be much larger than the cross sectional surface area of the direct imaging digital device.

In addition, a tapered channel may be formed from the opening of the first housing segment towards the second housing segment, so as to enable the direct imaging digital device to be able to move conveniently; a through hole that is smaller in size compared the opening may be formed in between the first housing segment and the second housing segment; a covered channel covers the surface of the direct imaging digital device, and this is formed by the second housing segment that is in alignment with the through hole. The diameter of the through hole may be approximately equal to the cross sectional surface area of the direct imaging digital device.

In accordance with a preferred exemplary embodiment of the present invention, the first sheet structure and the second sheet structure of the bag structure may be mainly made up of an elastic material, to enable the second housing segment to expand, and subsequently changing the size of the covered channel, subsequent to the expansion of the direct imaging digital device.

In addition to the above, the sheath of the present invention may further include a positioning device that closes or shrinks the opening, and whereby the positioning device may be in connection with the first housing segment of the bag structure. In accordance with a preferred exemplary embodiment of the present invention, the positioning device may be made up of one of an adhesive component, a fastening component, a component for a hook or strap assembly, or a belted component.

Moreover, the direct imaging digital device further includes an additional transmission line, and whereby the transmission line of the direct imaging digital device passes through the opening, and the transmission line of the direct imaging digital device acts as an axis for the first housing segment; the first housing segment encircles the axis and forms a belt pattern.

Finally, the one side of the tapered channel further includes an open pattern that extends from the through hole to the opening, and the open pattern forms a continuous opening collectively and at the same time with the opening. Or, the periphery of the opening further includes at least a rip that is positioned from the opening to the covered channel, to enable the periphery of the opening to form a non-continuous pattern.

The distinguishing technical feature of the present invention is to provide a sheath for a disposable dental direct imaging digital device, and in particular, to provide a sheath for suitably placing a direct imaging digital device of different sizes. The disposable sheath for a dental direct imaging digital device of the present invention may have the feature of having a tapered end from the opening of the sheath to the through hole which is located in the central region of the sheath. Moreover, relative to the through hole, the opening may be larger. Accordingly, the user may be able to slide and place the direct imaging digital device into the sheath quickly and easily, without the need to carefully aim the direct imaging digital device to the sheath. In addition, the design of the sheath is such that it has a tapered end to enable the easy guidance of the direct imaging digital device; and the sheath may be also designed to have a positioning device on one end, in order to shrink or close the opening of the sheath, and also to prevent the direct imaging digital device from falling out of the sheath. Moreover, the sheath may be also designed as a disposable sheath that is only used once, in order to ensure the personal hygiene and safety of the individual patients.

BRIEF DESCRIPTION OF THE DRAWINGS

The present invention can be understood in more detail by reading the subsequent detailed description in conjunction with the examples and preferred exemplary embodiments made to the accompanying drawings, wherein.

DETAILED DESCRIPTION OF THE PREFERRED EMBODIMENT

The accompanying drawings are included to provide a further understanding of the invention, and are incorporated in and constitute a part of this specification. The drawings illustrate the preferred exemplary embodiments of the invention and, together with the description, serve to explain the principles of the invention.

Figure 2:
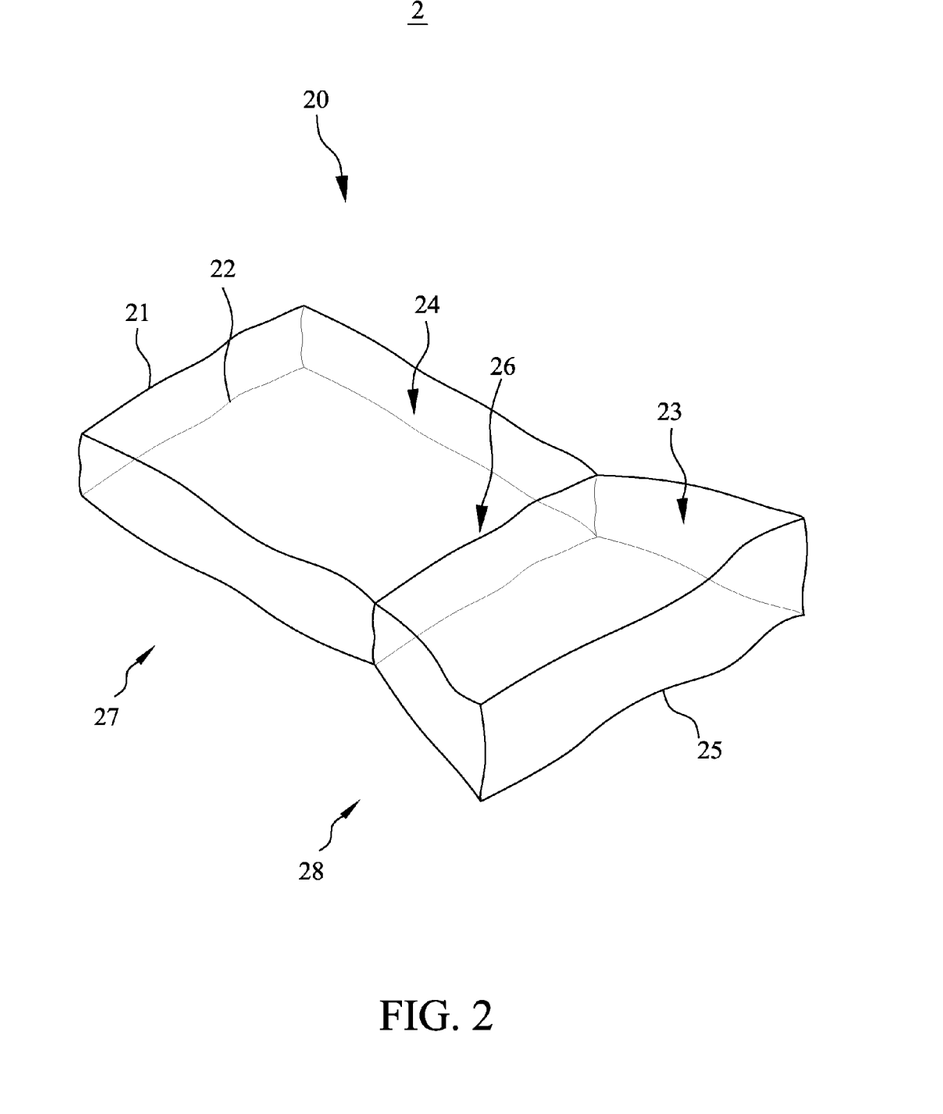
FIG. 2 is a three-dimensional schematic diagram illustrating a sheath for a disposable dental direct imaging digital device in accordance with a first preferred exemplary embodiment of the present invention.

As shown in FIG. 2, in accordance with a preferred exemplary embodiment of the present invention, besides being used mainly for encapsulating the dental direct imaging digital device 1, the sheath 2 of the present invention may help to prevent the saliva of the patients coming in direct contact with the direct imaging digital device 1 when the patients are undergoing X-ray imaging. As such, the direct imaging digital device 1 may be kept clean, since the sheath 2 may be removed and thrown away subsequent to completion of the X-ray imaging procedure. Accordingly, the direct imaging digital device 1 may also be re-used.

As shown in the Figs, the sheath 2 may also be a bag structure 20 that encapsulates a direct imaging digital device 1 in its interior. The sheet body 20 may be mainly made up of a first sheet body 21 that is in connection with a peripheral edge of a symmetrical second sheet body 22.

The bag structure 20 includes a first housing segment 23 that encapsulates the direct imaging digital device 1, and includes a second housing segment 24 that has the functions of positioning and encapsulating the direct imaging digital device 1. One end of the first housing segment 23 has an opening 25 that is in connection with the external space. A through hole 26 that is in connection with the second housing segment 24 may be found on the other end of the first housing segment 23. A covered channel 27 may be formed by the second housing segment 24 that is in alignment with the through hole 26.

In accordance with a preferred exemplary embodiment of the present invention, a tapered channel 28 may be formed from the opening 25 of the first housing segment 23 towards the second housing segment 24. As such, the size and pore diameter of the through hole 26 may be smaller than the size and pore diameter and size of the opening 25; and furthermore, the pore diameter and size of the through hole 26 may be approximately the same as the cross sectional surface area of the direct imaging digital device.

Due to the fact that the pore diameter and size of the opening 25 may be far greater than the cross sectional surface area of the direct imaging digital device 1, as such, the user may be able to easily place the direct imaging digital device 1 into the bag structure 20, through the opening 25 having a wide surface area. In addition, with the presence of the sheath of the present invention, the use of a traditional sheath which needed time-consuming and accurate aiming of the direct imaging digital device to the sheath may be no longer needed, and also enabling the direct imaging digital device to be encapsulated.

Besides the above, in accordance with a preferred exemplary embodiment of the present invention, in general, the direct imaging digital devices 1 that are used in dentistry may have various sizes, the lengths of these may vary and generally be 30 mm, 36 mm, 42 mm as well as 44.5 mm; and the widths of these direct imaging digital devices 1 may also vary and may be 22 mm, 25 mm, 30 mm and 32 mm. However, the thickness of the direct imaging digital devices 1 may be generally between 5.3 mm to 8.3 mm.

In order to enable the sheath 2 of the present invention to be used with the above-mentioned direct imaging digital device 1 of different sizes, the first sheet body 21 and the second sheet body 22 are made up of an elastic material. When the direct imaging digital device 1 moves from the first housing segment 23 into the second housing segment 24, the second housing segment 24 will expand in response to the presence of the direct imaging digital device 1, and the covered channel 27 may be caused to gradually expand and therefore the size of the covered channel 27 may also be changed subsequently. Lastly, the covered channel 27 will fully encapsulate the whole direct imaging digital device 1, and as such preventing the direct contact of the direct imaging digital device 1 with any external foreign objects.

Figure 3:
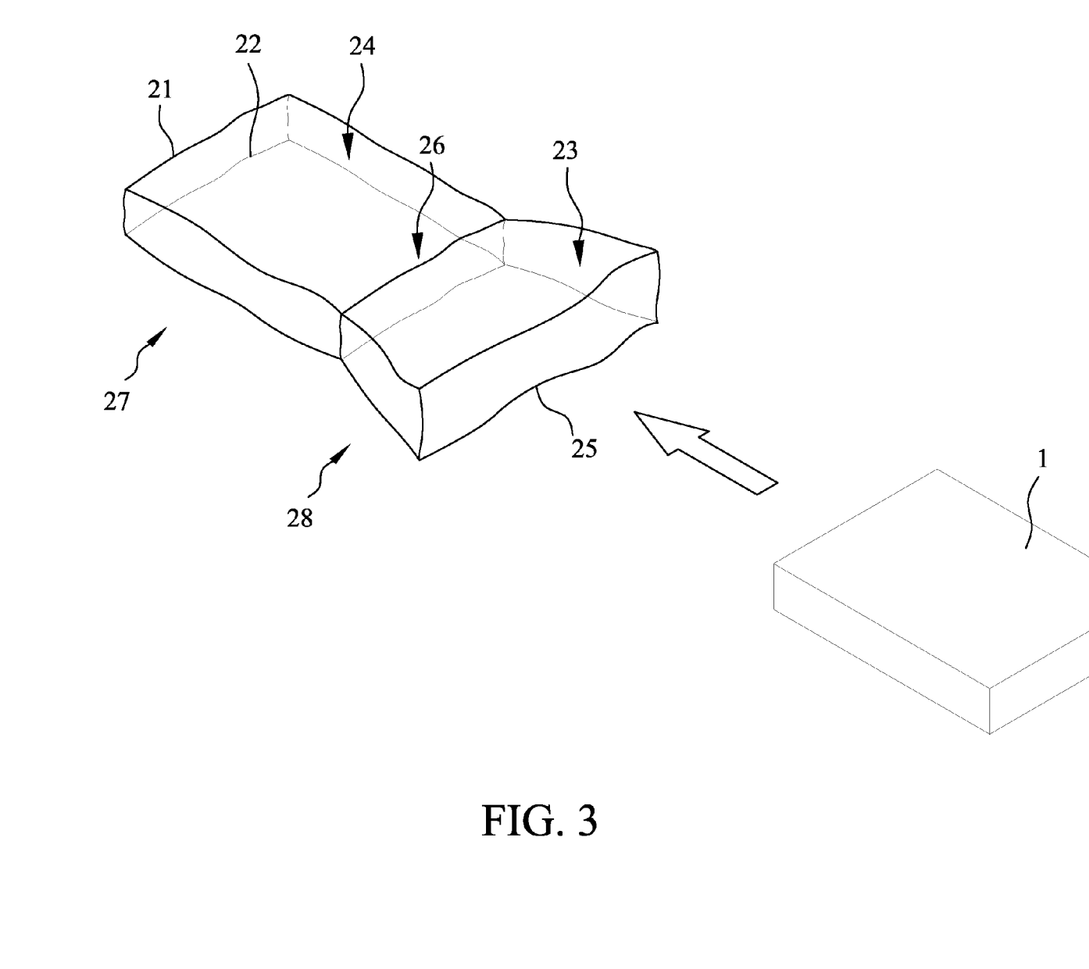
FIG. 3 is a three-dimensional schematic diagram illustrating a positioning device inserted into the sheath of FIG. 2 in accordance with the first preferred exemplary embodiment of the present invention.

As shown in FIG. 3, the direct imaging digital device 1 may slide successfully into the sheath 2 of the present invention through the opening 25, and finally achieving the effects of positioning and encapsulation of the direct imaging digital device 1.

Figure 4:
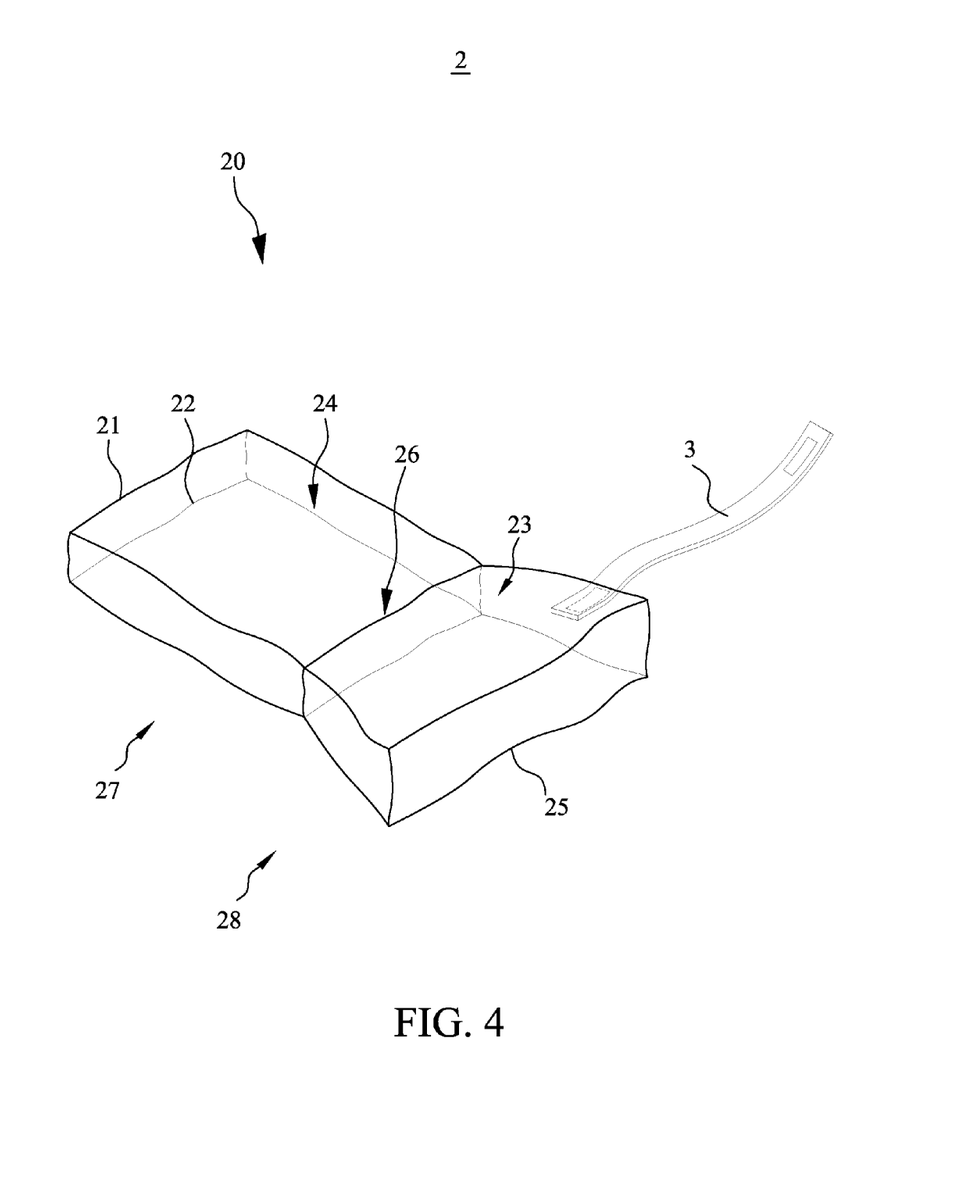
FIG. 4 is a three-dimensional schematic diagram illustrating the positioning device placed inside the sheath of FIG. 2 in accordance with the first preferred exemplary embodiment of the present invention.

As can be seen in FIG. 4, besides having a bag structure 20, the sheath 2 of the present invention may also include a positioning device 3. Due to the fact that the description for the bag structure 20 may be the same as the foregoing, it is therefore not repeated here. In accordance with a preferred exemplary embodiment of the present invention, the positioning device 3 may be used mainly for closing the opening 25, or the positioning device 23 may also be used for shrinking the first housing segment 23, to enable the covered channel 27 to form a closed space. As shown in the Figs, the positioning device 3 of the present invention has an adhesive component, whereby one end of the adhesive component may be an adhesive end, and the other end of the adhesive component has an undertaking end that complements the adhesive end.

However, the above-mentioned positioning device 3 only acts as a convenient embodiment of the present invention, and it is not meant to limit the design of the structure of the present invention in any way. Moreover, the positioning device 3 may also be designed as a fastening component, a component for a hook or strap assembly, or designed as a belted component and the like. The aforesaid various components are intended as a means for producing a positioning effect.

Figure 5:
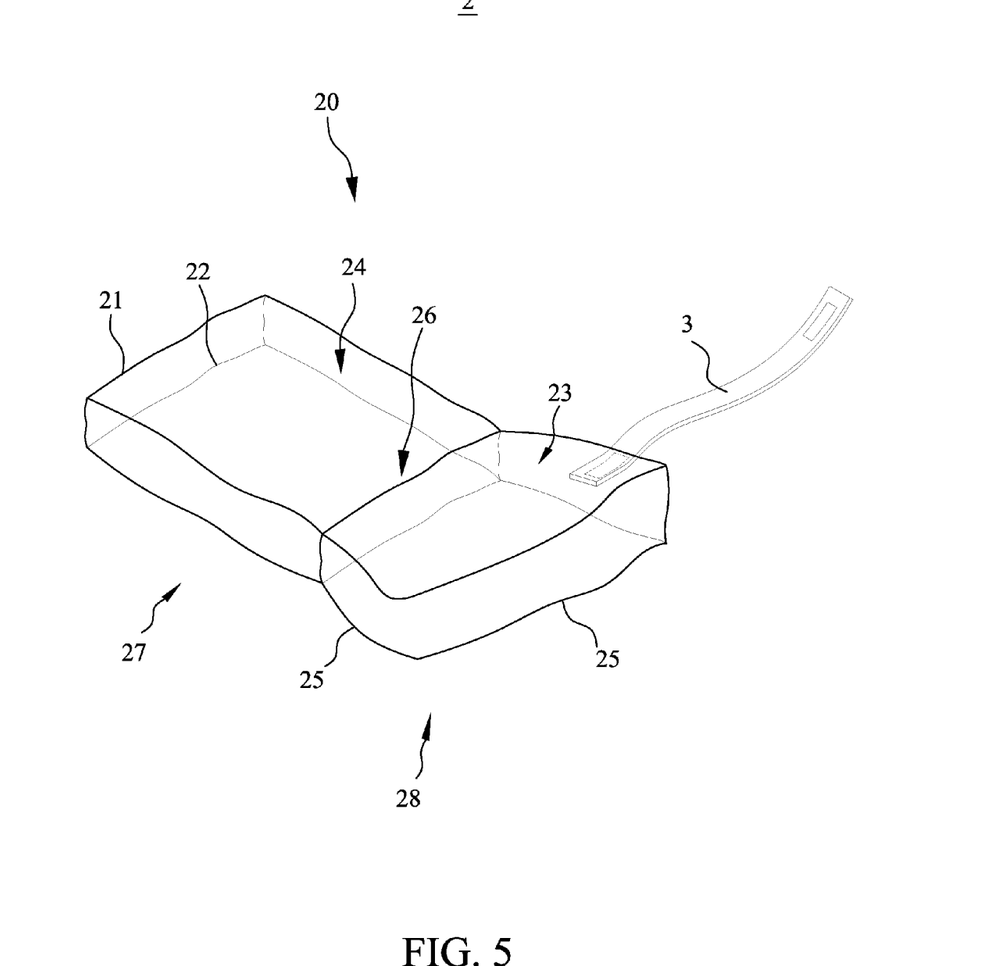
FIG. 5 is a three-dimensional schematic diagram illustrating the sheath for a disposable dental direct imaging digital device in accordance with a second preferred exemplary embodiment of the present invention.

As shown in FIG. 5, the opening 25 may be parallel to the open pattern that is located on the other end of the sheath 2. However, as compared with the opening 25 that has been illustrated in accordance with the first preferred exemplary embodiment of the present invention, and in accordance with a second preferred exemplary embodiment of the present invention, the opening 25 may be designed to be on one side of the tapered channel 28, and this opening 25 may also be designed as an open-state opening, and as such, increasing the ease of use and convenience when users insert the direct imaging digital device 1 into the sheath having a larger surface area.

Figure 6:
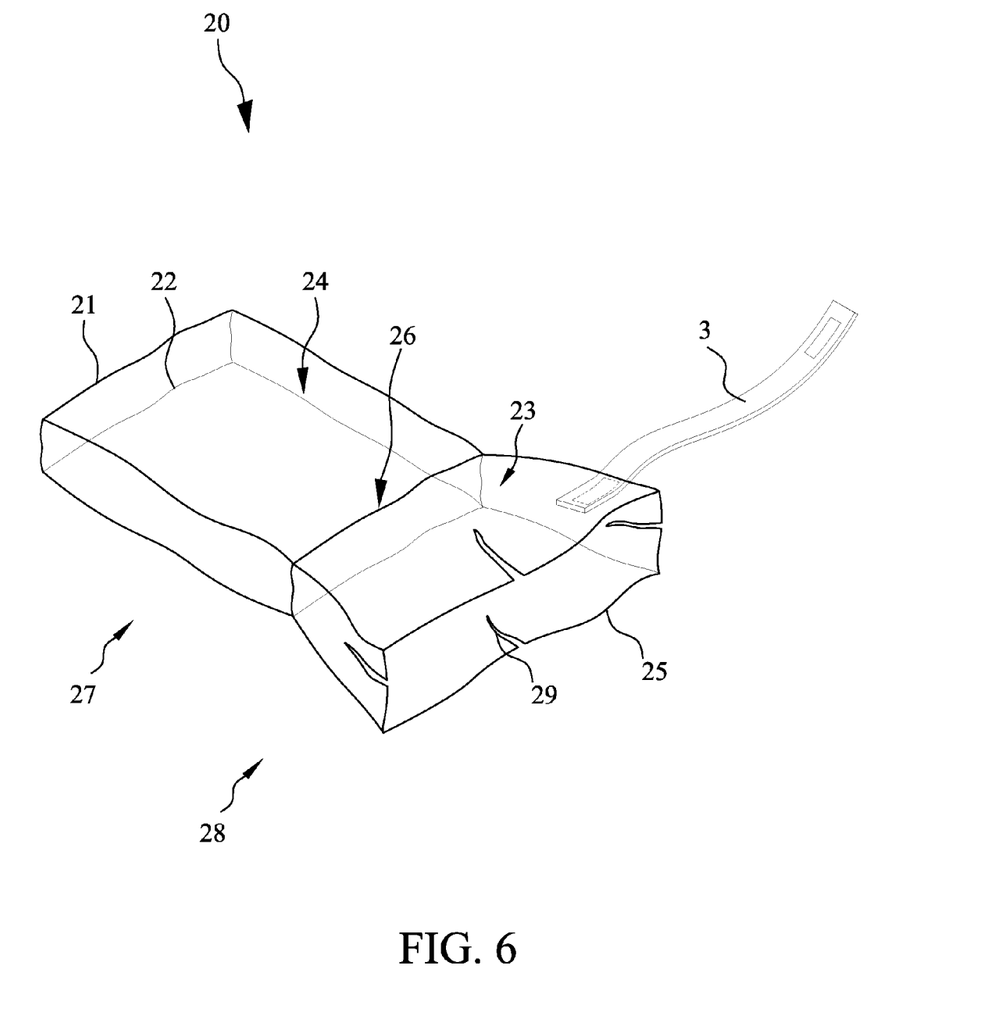
FIG. 6 is a three-dimensional schematic diagram illustrating the sheath for a disposable dental direct imaging digital device in accordance with a third preferred exemplary embodiment of the present invention.

Referring to FIG. 6, and in accordance with a third preferred exemplary embodiment of the present invention, as compared with the opening 25 as illustrated in the first preferred exemplary embodiment of the present invention, the opening 25 of this preferred exemplary embodiment having a complete rectangular-shaped opening may include at least one rip 29 such that the rectangular-shaped opening 25 has at least one rip 29. As shown in FIG. 6, the opening 25 may include a rip 29 in four different directions. The rip 29 may be formed from the opening 25 towards the covered channel 27. As such, the sheath 2 including the opening 25 with the rip 29 may enable different sizes of the direct imaging digital device 1 to be inserted into the sheath 2 of the present invention. Therefore, the ease of use and convenience may be increased based on the third preferred exemplary embodiment of the present invention.

Figure 7:
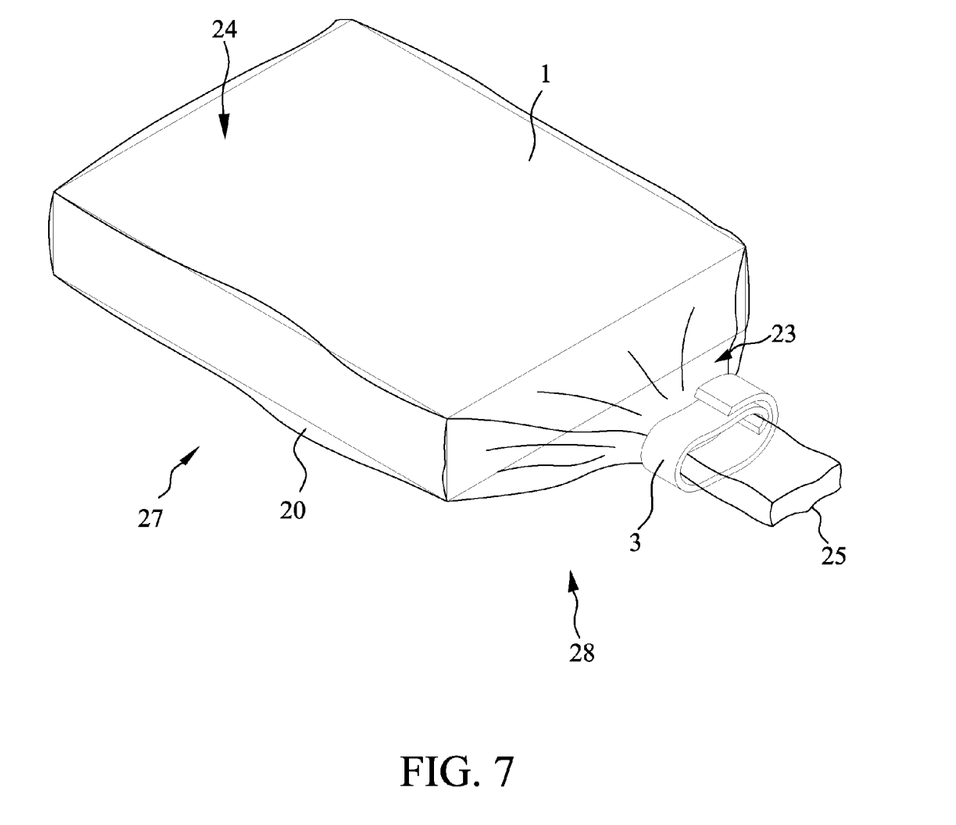
FIG. 7 is a schematic diagram illustrating the direct imaging digital device covered by the positioning device in accordance with the preferred exemplary embodiments of the present invention.

As shown in FIG. 7, the direct imaging digital device 1 has been inserted into the second housing segment 24 of the sheath 2 in accordance with the preferred exemplary embodiment of the present invention. In the meantime the covered channel 27 may be covered by a positioning device 3. Moreover, the positioning device 3 of the sheath 2 of the present invention may encircle and tighten the first housing segment 23, such that a belt pattern may be formed by pressing the positioning device 3 of the sheath 2 of the present invention. As such, the direct imaging digital device 1 inserted into the sheath 2 of the present invention may not slide out of the sheath 2 of the present invention.

Figure 8:
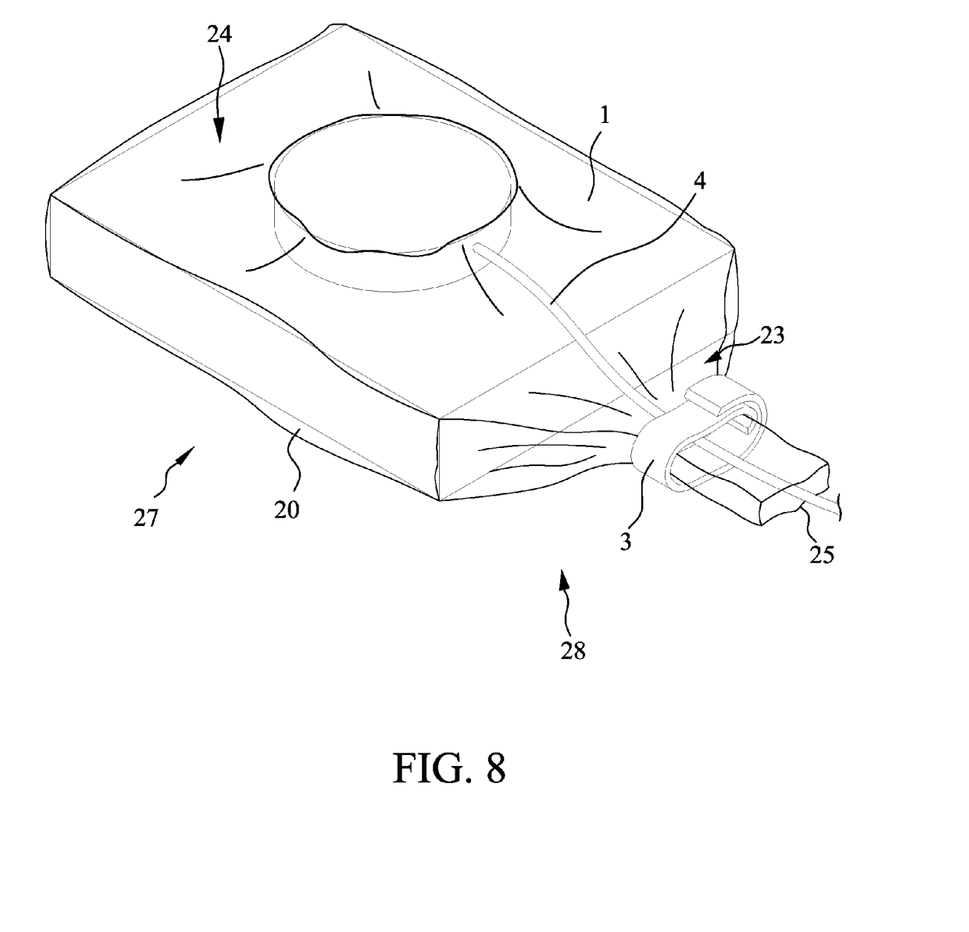
FIG. 8 is a schematic diagram illustrating a transmission line incorporated into the direct imaging digital device in accordance with the preferred exemplary embodiments of the present invention.

As shown in FIG. 8, as compared with FIG. 7, the direct imaging digital device 1 of the present invention may further include a transmission line 4. The transmission line 4 may be in connection with the direct imaging digital device 1 through a slot and a socket corresponding to the slot. The connection between the transmission line 4 and the direct imaging digital device 1 may be easily assembled by a similar connection terminal principle, and may also be simply disassembled. In accordance to another embodiment of the present invention, the transmission line 4 and the direct imaging digital device 1 may be integrated as one piece. When the direct imaging digital device 1 having the transmission line 4 is inserted into the sheath 2 of the present invention, the transmission line 4 may pass through the opening 25, and the direct imaging digital device 1 having the transmission line 4 may be covered by the second housing segment 24. Accordingly, the opening 25 of the first housing segment 23 may be tightened around the axis of the transmission line 4 such that the transmission line 4 at the first housing segment 23 may also be covered by the positioning device 3 at the same time.

Although the preferred exemplary embodiments of the present invention have been described with reference to the preferred exemplary embodiments thereof, it may be apparent to those ordinarily skilled in the art that a variety of modifications and changes may be made without departing from the scope of the present invention which is intended to be defined by the appended claims.

What is claimed is:

1. A disposable sheath for a dental direct imaging digital device, comprising
   a first sheet body that is in connection with a peripheral edge of a symmetrical second sheet body, and forming a bag structure with an opening, wherein
   a direct imaging digital device is positioned in the interior of the bag structure;
   a first housing segment that is in connection with an opening exists on one end of the bag structure, the other end of the first housing segment is in connection with a second housing segment, wherein
   a size of the opening is larger than a sectional surface area of the direct imaging digital device;
   a tapered channel is formed from the opening of the first housing segment towards the second housing segment, enabling a through hole that is smaller in size compared the opening to be formed in between the first housing segment and the second housing segment, and
   a covered channel is formed by the second housing segment that is in alignment with the through hole,
   the first sheet structure and the second sheet structure of the bag structure comprise an elastic material, enabling the second housing segment to expand, and subsequently changing the size of the covered channel, following the expansion of the direct imaging digital device.

2. The disposable sheath for a dental direct imaging digital device according to claim 1, wherein the diameter of the through hole is approximately equal to the cross sectional surface area of the direct imaging digital device.

3. The disposable sheath for a dental direct imaging digital device according to claim 1, wherein the sheath further comprises a positioning device that closes or shrinks the opening, and wherein the positioning device is in connection with the first housing segment of the bag structure.

4. The disposable sheath for a dental direct imaging digital device according to claim 3, wherein the positioning device comprises one of an adhesive component, a fastening component, a component for a hook or strap assembly, or a belted component.

5. The disposable sheath for a dental direct imaging digital device according to claim 1,
   wherein the direct imaging digital device further comprises an additional transmission line, and
   wherein the transmission line of the direct imaging digital device passes through the opening, and the transmission line of the direct imaging digital device acts as an axis for the first housing segment, the first housing segment encircles the axis and forming a belt pattern.

6. A disposable sheath for a dental direct imaging digital device, comprising
   a first sheet body that is in connection with a peripheral edge of a symmetrical second sheet body, and forming a bag structure with an opening, wherein
   a direct imaging digital device is positioned in the interior of the bag structure;
   a first housing segment that is in connection with an opening exists on one end of the bag structure,
   the other end of the first housing segment is in connection with a second housing segment, wherein a size of the opening is larger than a sectional surface area of the direct imaging digital device;
   a tapered channel is formed from the opening of the first housing segment towards the second housing segment, enabling a through hole that is smaller in size compared the opening to be formed in between the first housing segment and the second housing segment, and
   a covered channel is formed by the second housing segment that is in alignment with the through hole, wherein one side of the tapered channel further comprises an open pattern that extends from the through hole to the opening, and the open pattern forms a continuous opening collectively with the opening.

7. The disposable sheath for a dental direct imaging digital device according to claim 6, wherein the diameter of the through hole is approximately equal to the cross sectional surface area of the direct imaging digital device.

8. The disposable sheath for a dental direct imaging digital device according to claim 6,
   wherein the sheath further comprises a positioning device that closes or shrinks the opening, and
   wherein the positioning device is in connection with the first housing segment of the bag structure.

9. The disposable sheath for a dental direct imaging digital device according to claim 6,
   wherein the direct imaging digital device further comprises an additional transmission line, and
   wherein the transmission line of the direct imaging digital device passes through the opening, and the transmission line of the direct imaging digital device acts as an axis for the first housing segment, the first housing segment encircles the axis and forming a belt pattern.

10. A disposable sheath for a dental direct imaging digital device, comprising
    a first sheet body that is in connection with a peripheral edge of a symmetrical second sheet body, and forming a bag structure with an opening, wherein a direct imaging digital device is positioned in the interior of the bag structure;
    a first housing segment that is in connection with an opening exists on one end of the bag structure, the other end of the first housing segment is in connection with a second housing segment, wherein a size of the opening is larger than a sectional surface area of the direct imaging digital device;
    a tapered channel is formed from the opening of the first housing segment towards the second housing segment, enabling a through hole that is smaller in size compared the opening to be formed in between the first housing segment and the second housing segment, and a covered channel is formed by the second housing segment that is in alignment with the through hole, wherein the periphery of the opening further comprises at least a rip that is positioned from the opening to the covered channel, to enable the periphery of the opening to form a non-continuous pattern.

11. The disposable sheath for a dental direct imaging digital device according to claim 10, wherein the diameter of the through hole is approximately equal to the cross sectional surface area of the direct imaging digital device.

12. The disposable sheath for a dental direct imaging digital device according to claim 10, wherein the sheath further comprises a positioning device that closes or shrinks the opening, and wherein the positioning device is in connection with the first housing segment of the bag structure.

13. The disposable sheath for a dental direct imaging digital device according to claim 10, wherein the direct imaging digital device further comprises an additional transmission line, and wherein the transmission line of the direct imaging digital device passes through the opening, and the transmission line of the direct imaging digital device acts as an axis for the first housing segment, the first housing segment encircles the axis and forming a belt pattern.

* * * * *